United States Patent
Mori et al.

(10) Patent No.: US 9,408,783 B2
(45) Date of Patent: Aug. 9, 2016

(54) DENTAL GYPSUM POWDER

(71) Applicant: GC Corporation, Bunkyo-ku (JP)

(72) Inventors: Daizaburo Mori, Saitama (JP); Emiko Fukushima, Koshigayashi (JP); Haruhiko Horiuchi, Chibashi (JP)

(73) Assignee: GC CORPORATION, Bunkyo-ku (JP)

( * ) Notice: Subject to any disclaimer, the term of this patent is extended or adjusted under 35 U.S.C. 154(b) by 120 days.

(21) Appl. No.: 14/228,676

(22) Filed: Mar. 28, 2014

(65) Prior Publication Data

US 2014/0296369 A1  Oct. 2, 2014

(30) Foreign Application Priority Data

Mar. 28, 2013 (JP) ................. 2013-069157

(51) Int. Cl.
*A61K 6/06* (2006.01)
*A61K 6/083* (2006.01)

(52) U.S. Cl.
CPC ............. *A61K 6/0835* (2013.01); *A61K 6/0625* (2013.01)

(58) Field of Classification Search
CPC .................................................. A61K 6/0625
See application file for complete search history.

(56) References Cited

U.S. PATENT DOCUMENTS

| | | | |
|---|---|---|---|
| 4,526,619 A | 7/1985 | Ohi et al. | |
| 4,647,311 A | 3/1987 | Ohi et al. | |
| 2004/0187741 A1 | 9/2004 | Liu et al. | |

FOREIGN PATENT DOCUMENTS

| | | |
|---|---|---|
| DE | 20 2010 006 531 U1 | 9/2010 |
| JP | 2001-031457 A | 2/2001 |
| JP | 3584564 B2 | 11/2004 |
| JP | 2006-282435 A | 10/2006 |

OTHER PUBLICATIONS

Extended European Search Report issued Jun. 17, 2014 in Patent Application No. 14001162.8.

"Melflux 5581 F High-performance superplasticizer for cement based construction materials", BASF, Technical Data Sheet, XP002725301, Mar. 2010, pp. 1-2.

"Melflux AP 101 F High-performance superplasticizer for cement based construction materials", BASF, Technical Data Sheet, XP002725322, Jan. 2009, pp. 1-2.

*Primary Examiner* — Michael Pepitone
(74) *Attorney, Agent, or Firm* — Oblon, McClelland, Maier & Neustadt, L.L.P.

(57) ABSTRACT

Provided is a dental gypsum powder having flowability, setting time, and strength of a set material that are suitable for producing a dental model. The dental gypsum powder contains 100 parts by weight of gypsum hemihydrate, 2 to 4 parts by weight of gypsum dihydrate, from 0.5 to 3 parts by weight of potassium sulfate, from 0.05 to 0.8 parts by weight of a polycarboxylate water reducing agent, and not contain more than 0.3 parts by weight of other additives. It is preferred that the amount of the polycarboxylate water reducing agent is from 0.15 to 0.3 parts by weight per 100 parts by weight of gypsum hemihydrate, and the amount of the potassium sulfate is from 25% by weight to the same amount of the amount of the gypsum dihydrate.

11 Claims, No Drawings

DENTAL GYPSUM POWDER

CROSS-REFERENCE TO RELATED APPLICATION

This application claims priority to Japanese Patent Application No. 2013-069157, filed Mar. 28, 2013.

BACKGROUND OF THE INVENTION

1. Field of the Invention

The present invention relates to a dental gypsum powder to be used for producing a dental model, forming a set material through kneading with water. More specifically, the invention relates to a dental gypsum powder having flowability on kneading, setting time, and strength of a set material that are suitable for dental use.

2. Description of the Conventional Art

In the field of dentistry, dental gypsum has been used for producing a model simulating an oral cavity, which is used in production of various dental prostheses to be installed in an oral cavity such as an inlay, a crown, a bridge, a partial denture and a complete denture.

The dental gypsum is generally available in the form of powder containing α-gypsum hemihydrate (hard gypsum) and/or β-gypsum hemihydrate (calcined gypsum), which are gypsum hemihydrate, as a major component. A dentist or a dental technician places prescribed amounts of dental gypsum powder and water for kneading in a small rubber bowl and kneads them with a dedicated spatula to prepare a gypsum slurry, and the gypsum slurry is then cast and set in a mold having an impression of an oral cavity, thereby producing a working model, a maxillary model and the like. A dental prosthesis is produced based on the working model, maxillary model and the like.

Accordingly, the dental gypsum is required to have accuracy capable of reproducing details of an oral cavity and is simultaneously required to have such a strength that prevents the reproduced details from being broken or damaged. The amount of water mixed is necessarily suppressed to a certain extent for ensuring the strength, and therefore a slurry of ordinary dental gypsum has a relatively high viscosity.

In view of the workability of the dental gypsum to be cast and set in a mold, a slurry of the dental gypsum is demanded to have flowability capable of flowing into the details of the mold. Furthermore, it is important to prevent air bubbles from contaminating into the slurry on kneading the dental gypsum powder and water since air bubbles having a diameter of approximately from 0.2 to 3 mm in the slurry may reduce the accuracy of the model. However, a slurry of ordinary dental gypsum is liable to be contaminated with air bubbles due to the high viscosity thereof as described above.

As a method for enhancing flowability of a composition kneaded with water, the use of a large powder-water ratio, which is the ratio of a kneading liquid to the powder, has been generally known. When the powder-water ratio is increased, however, there is a problem that the density of the set material is decreased after setting, and thus the mechanical strength thereof is decreased. For addressing the problem, it has been known in the field of building concrete that a water reducing agent or an AE water reducing agent is added to enhance flowability (see, for example, PTLs 1 to 3).

A water reducing agent is such a substance that facilitates kneading of powder and liquid to decrease the amount of water for kneading, thereby enhancing the strength of the composition after setting, and known examples thereof include lignin sulfonate, an oxycarboxylate salt, a naphthalenesulfonate salt, a melaminesulfonate salt, a polystyrenesulfonate salt and a polycarboxylate salt, which have a surface activation function. The use of these water reducing agent mixed decreases the viscosity of the slurry without changing the powder-water ratio, and thus the flowability may be improved to provide better kneading property and workability. The AE admixture (air entraining admixture) is a substance that has a function of dispersing minute independent air bubbles over the set material, in addition to the effects of the water reducing agent.

However, the use of the ordinary water reducing agent in dental gypsum powder considerably delays the setting thereof, and thus the ordinary water reducing agent has not been used in the field of dentistry, which requires a short setting time, for example, the set material is to be taken out from an impression within 5 minutes.

PTL 1
  Japanese Patent No. 3,584,564
PTL 2
  JP-A-2001-31457
PTL 3
  JP-A-2006-282435

SUMMARY OF THE INVENTION

An object of the invention is to provide an excellent dental gypsum powder having flowability on kneading, a setting time, and a strength of a set material that are suitable in the field of dentistry.

Means for Solving the Problem

As a result of earnest investigation made by the present inventors, it has been found that the aforementioned and other objects are achieved by mixing specific amounts of gypsum dihydrate, potassium sulfate and a polycarboxylate water reducing agent against gypsum hemihydrate, and suppressing the other additives to a specific amount, and thus the invention has been completed.

According to one aspect of the invention, a dental gypsum powder is provided that contains 100 parts by weight of gypsum hemihydrate, from 2 to 4 parts by weight of gypsum dihydrate, from 0.5 to 3 parts by weight of potassium sulfate, from 0.05 to 0.8 parts by weight of a polycarboxylate water reducing agent, and not contain more than 0.3 parts by weight of other additives.

In preferred embodiments of the invention, the amount of the polycarboxylate water reducing agent is from 0.15 to 0.3 part by weight per 100 parts by weight of gypsum hemihydrate, and the amount of the potassium sulfate is from 25% by weight to the same amount of the amount of the gypsum dihydrate.

Effect of the Invention

The dental gypsum powder according to the aspect of the invention has flowability on kneading, a setting time, and a strength of a set material that are suitable in the field of dentistry.

DETAILED DESCRIPTION OF PREFERRED EMBODIMENTS

Embodiments of the invention will be described in detail below, but the invention is not limited to the embodiments.

A dental gypsum powder according to the embodiment of the invention contains a polycarboxylate water reducing agent, which is selected from among water reducing agents that have not been used in ordinary dental gypsum powder. The use thereof not only facilitates kneading of powder and liquid, but also disperses minute independent air bubbles over the set material.

The polycarboxylate water reducing agent may be selected from those having been used mainly in the field of building concrete, and examples thereof include a water soluble salt of a copolymer of a linear olefin having 5 or 6 carbon atoms and an ethylenic unsaturated dicarboxylic anhydride, a copolymer of polyethylene glycol monoallyl ether and unsaturated dicarboxylic acid, a copolymer of polyalkylene glycol mono (meth)acrylic ester and (meth)acrylic acid, a copolymer of (meth)acrylic acid amide having a sulfone group at an end thereof, an acrylate ester and (meth)acrylic acid, a copolymer of a monomer having a sulfone group such as vinyl sulfonate, aryl sulfonate or methacryl sulfonate, (meth)acrylic acid, and another monomer, a copolymer of a monomer having an aromatic ring substituted with a sulfone group and maleic acid, and a quarterpolymer of a monomer having a sulfone group at an end thereof, a polyalkylene glycol mono(meth) acrylic ester, a polyalkylene glycol mono(meth) acrylic ether and (meth)acrylic acid.

The amount of the polycarboxylate water reducing agent mixed is from 0.05 to 0.8 parts by weight, preferably from 0.15 to 0.3 parts by weight, and more preferably from 0.15 to 0.25 parts by weight, per 100 parts by weight of the gypsum hemihydrate. When the amount of the water reducing agent is less than 0.05 parts by weight, the advantageous effects of the invention may not be sufficiently exhibited, and when the amount thereof exceeds 0.8 parts by weight, no further contribution to the flowability may not be obtained, but the durability after setting may be deteriorated, and the setting time may be delayed. The reducing agent may be mixed in any form, for example, in the form of a suspension liquid, powder or particle, and may be mixed at the time of dry-mixing of powder.

The dental gypsum powder according to the embodiment of the invention may contain the particular reducing agent described above in dental gypsum powder containing gypsum hemihydrate as a major component, which has been used in ordinary dental gypsum powder. Examples of the gypsum hemihydrate include α-gypsum hemihydrate, β-gypsum hemihydrate, and a mixture of α-gypsum hemihydrate and β-gypsum hemihydrate.

The dental gypsum powder according to the embodiment of the invention contains the specific amount of gypsum dihydrate. The use of gypsum dihydrate provides effects of acceleration of setting and increase of setting expansion. The amount of the gypsum dihydrate is from 2 to 4 parts by weight, preferably from 2 to 3.5 parts by weight, and more preferably from 2 to 3 parts by weight, per 100 parts by weight of the gypsum hemihydrate. When the amount of the gypsum dihydrate is less than 2 parts by weight, the setting may not be sufficiently accelerated, and when the amount exceeds 4 parts by weight, the flowability may be lowered, and the setting expansion may be increased, which result in deterioration of the accuracy.

Examples of the gypsum dihydrate include natural gypsum and chemical gypsum. Examples of the chemical gypsum include one that is freshly synthesized from sulfuric acid and calcium carbonate, but most kinds thereof are by-produced gypsum obtained as a by-product of various chemical reactions. The chemical gypsum generally has an average particle diameter of approximately from 30 to 60 µm, and gypsum dihydrate having an average particle diameter larger than 60 µm may also be used.

The dental gypsum powder according to the embodiment of the invention contains the specific amount of potassium sulfate. The use of potassium sulfate provides effects of accelerating the setting and suppressing the setting expansion. The amount of the potassium sulfate is from 0.5 to 3 parts by weight per 100 parts by weight of the gypsum hemihydrate. When the amount thereof is less than 0.5 parts by weight per 100 parts by weight of the gypsum hemihydrate, the effect of accelerating the setting may be insufficient, and when the amount exceeds 3 parts by weight, the setting may proceed too rapidly. The amount of the potassium sulfate is preferably from 0.15 to 0.3 parts by weight per 100 parts by weight of the gypsum hemihydrate. The amount of the potassium sulfate may also be determined in relation to the amount of the gypsum dihydrate. In this case, the amount of the potassium sulfate is preferably from 25% by weight to the same amount of the amount of the gypsum dihydrate, and thereby the setting expansion that is suitable for a dental model may be obtained.

The dental gypsum powder according to the embodiment of the invention may contain known additives, for example, a setting expansion preventing agent such as potassium tartrate, a colorant, a weight saving material, and a retarder such as a salt, e.g., a citrate salt, a borate salt and an acetate salt, and a water soluble polymer such as starch, gum arabic, carboxymethyl cellulose and gelatin. The amount of the additive mixed must be no more than 0.3 parts by weight per 100 parts by weight of the gypsum hemihydrate for exhibiting the effect of the water reducing agent.

The dental gypsum powder according to the embodiment of the invention may not contain a water reducing agent other than the polycarboxylate water reducing agent since the other water reducing agent may enhance the flowability but considerably delays the setting of the dental gypsum. Examples of the water reducing agent that may not be used in the invention include a naphthalene water reducing agent (such as a naphthalenesulfonic acid formalin condensate), a melamine water reducing agent (such as a melaminesulfonic acid formalin condensate) and an aminosulfonic acid water reducing agent (such as an aromatic aminosulfonic acid polymer).

The dental gypsum powder according to the embodiment of the invention is in the form of powder as similar to ordinary dental gypsum, and may be used, for example, in such a manner that a suitable amount of water, for example, from 18 to 28 parts by weight per 100 parts by weight of the dental gypsum powder is added to the dental gypsum powder to form a slurry, which is cast and set into an arbitrary shape, thereby producing a dental model.

Examples of the invention will be described in detail below, but the invention is not limited to the examples.

EXAMPLE

Gypsum dihydrate, a water reducing agent, potassium sulfate and an additive were placed in a pot mill and mixed for 20 minutes, thereby producing dental gypsum powder.

The formulations of Examples 1 to 8 are shown in Table 1, and the formulations of Comparative Examples 1 to 16 are shown in Tables 2-1 and 2-2. The amounts of the ingredients shown in the tables are parts by weight.

Evaluation of Setting Time 100 g of the dental gypsum powder produced in Examples or Comparative Examples and 23 g of tap water were placed in a rubber bowl and mixed with a gypsum spatula to provide a slurry, which was then measured for the physical property (setting time) according to the method defined in JIS T6605 (Dental stone). The results obtained are shown in Tables 1 and 2.

Evaluation of Flowability 100 g of the dental gypsum powder produced in Examples or Comparative Examples and 23 g of tap water were placed in a rubber bowl and mixed with a gypsum spatula to provide a slurry, which was then measured for the physical property (flowability) according to the method defined in JIS T6601 (Dental gypsum-bonded casting investments). The results obtained are shown in Tables 1 and 2. The symbols showing the evaluation have the following meanings.

A: more than 60 mm
B: from 40 to 60 mm
C: less than 40 mm

Evaluation of Strength of Set Material after 5 Minutes 100 g of the dental gypsum powder produced in Examples or Comparative Examples and 23 g of tap water were placed in a rubber bowl and mixed with a gypsum spatula to provide a slurry. The slurry was then cast in an impression material, and after 5 minutes, a gypsum model was taken out from the impression material and measured for the physical property (strength) according to the method defined in JIS T6605 (Dental stone). The results obtained are shown in Tables 1 and 2. The symbols showing the evaluation have the following meanings.

A: more than 10 MPa
B: from 3 to 10 MPa
C: less than 3 MPa

TABLE 1

| | | Example | | | | | | | |
|---|---|---|---|---|---|---|---|---|---|
| | | 1 | 2 | 3 | 4 | 5 | 6 | 7 | 8 |
| α-Gypsum hemihydrate | | 100 | 100 | 100 | 100 | 100 | 100 | 100 | 100 |
| Gypsum dihydrate | | 3 | 3 | 2 | 3 | 3 | 4 | 3 | 3 |
| Polycarboxylate water reducing agent | Melflux 2651F | | | 0.3 | | | | | |
| | Melflux 4930F | 0.15 | | | | | | | |
| | Melflux 5581F | | 0.15 | | 0.2 | 0.2 | 0.25 | 0.2 | 0.2 |
| Modified polycarboxylate water reducing agent | Melflux AP101F | | | | | | | | |
| Naphthalenesulfonic acid water reducing agent | Powercon | | | | | | | | |
| Melaminesulfonic acid water reducing agent | NL-G400 | | | | | | | | |
| Potassium sulfate | | 2 | 3 | 0.5 | 1 | 2 | 2 | 1 | 2 |
| Sodium sulfate | | | | | | | 0.1 | | 0.1 |
| Magnesium sulfate | | | | | | | | | |
| Potassium tartrate | | | | | | | | | |
| Sodium tartrate | | | | | | | | | |
| Silicone oil | | | | | | | 0.001 | | |
| Setting time (min) | | 3 | 4 | 4.5 | 4.75 | 3.5 | 2.25 | 2.25 | 3.5 |
| Flowability | | A | A | B | A | A | A | A | B |
| Strength after 5 minutes | | B | B | B | B | B | B | A | A |

TABLE 2

| | | Comparative Example | | | | | | | |
|---|---|---|---|---|---|---|---|---|---|
| | | 1 | 2 | 3 | 4 | 5 | 6 | 7 | 8 |
| α-Gypsum hemihydrate | | 100 | 100 | 100 | 100 | 100 | 100 | 100 | 100 |
| Gypsum dihydrate | | 3 | 3 | 3 | 3 | 3 | 3 | 1.5 | |
| Polycarboxylate water reducing agent | Melflux 2651F | | | | | | | | |
| | Melflux 4930F | | | | | | | | |
| | Melflux 5581F | 0.2 | 0.2 | 0.6 | | | | | |
| Modified polycarboxylate water reducing agent | Melflux AP101F | | | | | | 0.2 | | |
| Naphthalenesulfonic acid water reducing agent | Powercon | | | | | 0.6 | | | |
| Melaminesulfonic acid water reducing agent | NL-G400 | | | | | | 0.6 | 0.2 | 0.2 |
| Potassium sulfate | | | | | 2 | 1 | 2 | 2 | 0.02 |
| Sodium sulfate | | | | | 0.6 | | | | 0.01 |
| Magnesium sulfate | | | | | | 0.1 | | | |
| Potassium tartrate | | 2 | | | | | | | |
| Sodium tartrate | | | 2 | | | | | | |
| Silicone oil | | | | | 0.1 | 0.1 | | | |
| Setting time (min) | | 5.5 | 20 | 5.5 | 5 | 6.25 | 2 | 6.5 | 15 |
| Flowability | | A | A | B | C | C | C | B | A |
| Strength after 5 minutes | | C | C | C | C | B | B | C | C |

| | | Comparative Example | | | | | | | |
|---|---|---|---|---|---|---|---|---|---|
| | | 9 | 10 | 11 | 12 | 13 | 14 | 15 | 16 |
| α-Gypsum hemihydrate | | 100 | 100 | 100 | 100 | 100 | 100 | 100 | 100 |
| Gypsum dihydrate | | 1.5 | 3 | 2 | 2 | 2 | 3 | 3 | 3 |

TABLE 2-continued

| | | | | | | | | | |
|---|---|---|---|---|---|---|---|---|---|
| Polycarboxylate water reducing agent | Melflux 2651F | 0.3 | | | | | | | |
| | Melflux 4930F | | | | | | | | |
| | Melflux 5581F | | | | | | | | |
| Modified polycarboxylate water reducing agent | Melflux AP101F | | | | | | | | |
| Naphthalenesulfonic acid water reducing agent | Powercon | | | | | | | | |
| Melaminesulfonic acid water reducing agent | NL-G400 | 1.2 | 5 | 0.2 | 0.2 | 0.2 | | 0.2 | 0.2 |
| Potassium sulfate | | 5 | 2 | 1 | 1 | 1 | 2 | 2 | 2 |
| Sodium sulfate | | 0.01 | | | | 1 | 0.5 | 0.5 | 0.8 |
| Magnesium sulfate | | | | | | | | | |
| Potassium tartrate | | | | | | | | | |
| Sodium tartrate | | | | | | | | | |
| Silicone oil | | | | | 0.1 | | 0.1 | 0.1 | 0.1 |
| Setting time (min) | | 20 | ≥20 | 6 | 6 | 20 | 4.5 | 2.25 | 2.75 |
| Flowability | | A | A | A | A | A | C | C | C |
| Strength after 5 minutes | | C | C | C | C | C | B | B | B |

In the tables, Melflux 2651F, Melflux 4930F and Melflux 5581F are each a polycarboxylate water reducing agent produced by BASF AG, Melflux AP101F is a modified polycarboxylate water reducing agent produced by BASF AG, Powercon is a naphthalenesulfonic acid water reducing agent produced by BASF AG, and NL-G400 is a melaminesulfonic acid water reducing agent produced by BASF AG.

It is understood from the results shown in Table 1 that Examples 1 to 8 show a setting time within 5 minutes and evaluation results of B or better for the flowability and the strength after 5 minutes. It is understood from the results shown in Tables 2-1 and 2-2 that Comparative Examples 1 to 3, in which the amount of the polycarboxylate water reducing agent is in the range of the invention, but the amount of additive exceeds 0.3 parts by weight, show a setting time exceeding 5 minutes and an evaluation result of C for the strength after 5 minutes, and Comparative Examples 4 to 16, in which no polycarboxylate water reducing agent is used as a water reducing agent, show an evaluation result of C for at least one of the flowability and the strength after 5 minutes, and thus Comparative Examples 1 to 16 are not favorable as dental gypsum powder.

What is claimed is:

1. A dental gypsum powder, comprising:
   100 parts by weight of gypsum hemihydrate;
   from 2 to 4 parts by weight of gypsum dihydrate;
   from 0.5 to 3 parts by weight of potassium sulfate; and
   from 0.05 to 0.8 parts by weight of a polycarboxylate water reducing agent;
   wherein:
   the dental gypsum power does not comprise more than 0.3 parts by weight of other additives; and
   the polycarboxylate water reducing agent comprises a water soluble salt selected from the group consisting of:
   a water soluble salt of a copolymer of a linear olefin having 5 or 6 carbon atoms and an ethylenic saturated dicarboxylic anhydride;
   a water soluble salt of a copolymer of polyethylene glycol monoallyl ether and unsaturated dicarboxylic acid;
   a water soluble salt of a copolymer of polyalkylene glycol mono(meth)acrylic ester and (meth)acrylic acid;
   a water soluble salt of a copolymer of (meth)acrylic acid amide having a sulfone group at an end thereof, an acrylate ester, and (meth)acrylic acid;
   a water soluble salt of a copolymer of a first monomer selected from vinyl sulfonate, aryl sulfonate, and methacryl sulfonate, a second monomer, and (meth)acrylic acid;
   a water soluble salt of a copolymer of a monomer having an aromatic ring substituted with a sulfone group and maleic acid; and
   a water soluble salt of a quaterpolymer of a monomer having a sulfone group at an end thereof a polyalkylene glycol mono(meth) acrylic ester, a polyalkylene glycol mono(meth) acrylic ether, and (meth)acrylic acid.

2. The dental gypsum powder according to claim 1, wherein the amount of the polycarboxylate water reducing agent is from 0.15 to 0.3 parts by weight per 100 parts by weight of gypsum hemihydrate.

3. The dental gypsum powder according to claim 1, wherein the amount of the potassium sulfate is from 25% by weight to the same amount of the amount of the gypsum dihydrate.

4. The dental gypsum powder according to claim 2, wherein the amount of the potassium sulfate is from 25% by weight to the same amount of the amount of the gypsum dihydrate.

5. The dental gypsum powder according to claim 1, wherein the polycarboxylate water reducing agent comprises a water soluble salt of a copolymer of a linear olefin having 5 or 6 carbon atoms and an ethylenic unsaturated dicarboxylic anhydride.

6. The dental gypsum powder according to claim 1, wherein the polycarboxylate water reducing agent comprises a water soluble salt of a copolymer of polyethylene glycol monoallyl ether and unsaturated dicarboxylic acid.

7. The dental gypsum powder according to claim 1, wherein the polycarboxylate water reducing agent comprises a water soluble salt of a copolymer of polyalkylene glycol mono(meth)acrylic ester and (meth)acrylic acid.

8. The dental gypsum powder according to claim 1, wherein the polycarboxylate water reducing agent comprises a water soluble salt of a copolymer of (meth)acrylic acid amide having a sulfone group at an end thereof, an acrylate ester, and (meth)acrylic acid.

9. The dental gypsum powder according to claim 1, wherein the polycarboxylate water reducing agent comprises a water soluble salt of a copolymer of a first monomer selected from vinyl sulfonate, aryl sulfonate, and methacryl sulfonate, a second monomer, and (meth)acrylic acid.

10. The dental gypsum powder according to claim 1, wherein the polycarboxylate water reducing agent comprises a water soluble salt of a copolymer of a monomer having an aromatic ring substituted with a sulfone group and maleic acid.

11. The dental gypsum powder according to claim 1, wherein the polycarboxylate water reducing agent comprises a water soluble salt of a quaterpolymer of a monomer having a sulfone group at an end thereof, a polyalkylene glycol mono(eth) acrylic ester, a polyalkylene glycol mono(meth) acrylic ether, and (meth)acrylic acid.

* * * * *